US007150734B2

(12) United States Patent
Lecointe

(10) Patent No.: US 7,150,734 B2
(45) Date of Patent: Dec. 19, 2006

(54) BAG FOR PACKAGING LIQUID BIOLOGICAL SUBSTANCES, HAVING AN INTEGRATED CANNULA

(75) Inventor: Pascal Lecointe, Saint Gregoire (FR)

(73) Assignee: Eurl Pig'Ins, Quebriac (FR)

( * ) Notice: Subject to any disclaimer, the term of this patent is extended or adjusted under 35 U.S.C. 154(b) by 489 days.

(21) Appl. No.: 10/380,269

(22) PCT Filed: Sep. 12, 2001

(86) PCT No.: PCT/FR01/02836

§ 371 (c)(1),
(2), (4) Date: Apr. 4, 2003

(87) PCT Pub. No.: WO02/22044

PCT Pub. Date: Mar. 21, 2002

(65) Prior Publication Data

US 2003/0163110 A1 Aug. 28, 2003

(30) Foreign Application Priority Data

Sep. 13, 2000 (FR) .................................. 00 11625

(51) Int. Cl.

| | |
|---|---|
| *A61B 19/00* | (2006.01) |
| *A61M 5/00* | (2006.01) |
| *B65D 30/22* | (2006.01) |
| *B65D 33/16* | (2006.01) |
| *B65D 39/00* | (2006.01) |

(52) U.S. Cl. ...................... 604/408; 604/403; 604/415; 604/416; 604/262; 383/38; 383/67; 383/94; 383/906

(58) Field of Classification Search ........ 604/403–410, 604/415, 905, 257, 262, 317; 128/DIG. 24; 600/33–35; 215/47; 383/906, 35, 38–40, 383/42, 59, 66–67, 93, 94; 206/216, 218, 206/828; 220/200, 255, 255.1, 62.11–62.12, 220/62.21
See application file for complete search history.

(56) References Cited

U.S. PATENT DOCUMENTS

| | | | | | |
|---|---|---|---|---|---|
| 2,894,510 | A | * | 7/1959 | Bellamy, Jr. | 604/408 |
| 3,986,506 | A | * | 10/1976 | Garber et al. | 604/406 |
| 3,991,912 | A | * | 11/1976 | Soto | 222/89 |
| 4,195,632 | A | * | 4/1980 | Parker et al. | 604/411 |
| 4,294,247 | A | * | 10/1981 | Carter et al. | 604/403 |
| 4,548,606 | A | * | 10/1985 | Larkin | 604/414 |
| 4,637,934 | A | * | 1/1987 | White | 426/117 |
| 4,854,737 | A | * | 8/1989 | Steer et al. | 383/127 |

(Continued)

FOREIGN PATENT DOCUMENTS

EP 0 480 798 A 4/1992

(Continued)

*Primary Examiner*—Patricia Bianco
(74) *Attorney, Agent, or Firm*—Foley & Lardner LLP

(57) ABSTRACT

A packaging bag for a liquid biological substance such as animal semen, including two walls made of plastic material joined in such a manner as to delimit a pouch for receiving the substance and, communicating with the pouch, an evacuation conduit whose end part, in the absence of opening of the bag, is closed by the joined walls, wherein, force-fitted in the conduit, a cannula being able to communicate with the pouch is provided, while a second end of the cannula is situated in the proximity of the end part of the conduit having a conical or substantially conical constriction, and wherein conduit communicates, over a part of its length, with at least one zone situated not far from the end part, in which the two walls are not joined.

13 Claims, 5 Drawing Sheets

U.S. PATENT DOCUMENTS

| | | | | |
|---|---|---|---|---|
| 5,391,163 | A | 2/1995 | Christine et al. | |
| 5,884,758 | A | 3/1999 | Houle et al. | |
| 6,149,579 | A * | 11/2000 | Lee | 600/35 |

FOREIGN PATENT DOCUMENTS

| | | | |
|---|---|---|---|
| EP | 0 945 106 | A | 9/1999 |
| GB | 2 003 449 | A | 3/1979 |
| MC | 2 488 | A | 11/1999 |
| WO | WO 94 22731 | A | 10/1994 |

* cited by examiner 1
2
3
4'
5
6
8
9
10
11
13
30
40'
41'
80
81
124
125
126
P
S 2
13
2
3
5
30
30
9
P
8
127

T
T
C
C
T
T
P
4'
5
5
6
3

BAG FOR PACKAGING LIQUID BIOLOGICAL SUBSTANCES, HAVING AN INTEGRATED CANNULA

BACKGROUND OF THE INVENTION (1) Field of the Invention

This invention relates to a bag for packaging biological liquid substance, such as animal semen.

It also relates to a strip formed by juxtaposing such bags.

(2) Related Art

Up to now, a number of types of packaging have been proposed for storing animal semen, especially that of porcine species.

Accordingly, there are tubes of supple plastic material which, once filled with semen and sealed, form what resembles a large tube of toothpaste. They comprise a distributor head which is connected to the body of the tube by a zone having a circular cross-section and large diameter.

This type of packaging has essentially two drawbacks. The first resides in the fact that it has a significant thickness due to the circular cross-section zone. The second drawback is due to the fact that the nozzle is closed during periods when it is not in use in such a fashion that it is necessary to cut it in order to be able to gain access to the semen and proceed with artificial insemination. This requires that the person carrying out the insemination operation have a cutting tool such as a pair of scissors. Now, the current trend is to work as quickly as possible and with a minimum of objects other than the bag and a wand, in order to limit the risks of loss of said objects and incidents that they could cause.

Relatively flat packaging bags are also known that are formed by joining two sheets of plastic material. A piece made of plastic material is applied to these bags which comprises a dispensing nozzle. These bags occupy less space than the aforesaid tubes but they nevertheless require an additional tool for opening the nozzle.

The existence of these problems makes clear that a generally accepted packaging of a bag is formed exclusively of two walls of joined plastic material so as to delimit a pouch for receiving said substance and, communicating with said pouch, an outlet conduit whose terminal part is, in the absence of opening the bag, closed off by said joined walls.

A slit arranged in the vicinity of the conduit, a peelable zone or a supplementary means makes it possible to open the outlet conduit without requiring the use of an additional tool.

And in view of artificial insemination, a wand is attached, said wand being comprised of a tube having at its end a solid foam plug or spiral.

A first possibility consists of connecting the wand directly to the bag by introducing into the conduit the end of the tube opposite to end having the plug.

This requires a certain dexterity insofar as the filled bag of semen is not rigid; it is soft and difficult to manipulate.

Furthermore, there is a plurality of wands with different external tube diameters. Therefore, it is necessary to provide different bags with conduit dimensions adapted to the wands with the risk of having the semen flow between the conduit and the wand.

However, when looking for conduit dimensions that match perfectly to those of the wand, there is the risk of piercing the bag at the time of introducing the wand, the end of which often has a sharp edge.

Furthermore, when the inseminated animals have freedom of movement, there is considerable risk that the bag may become disconnected.

A second possibility comprises connecting a coupling tube (called a coupler) to the conduit, then connecting the second end of the coupler to the wand.

This coupler comprises an additional part that the person performing the insemination should have within his reach and that is also apt to be mislaid.

Such a part is principally single-use, but it has been found that the same coupler could be used in several successive inseminations. Now, it has been frequently observed that semen migrates to inside the coupler or the bag during an insemination procedure. If the sow has a vaginal or uterine infection, the traces of semen left in the tube can contaminate the semen contained in the bag used for later insemination. This is unacceptable from the hygiene point of view.

GB-A-2 003 449 discloses a bag, in particular for storing blood platelets. In its different embodiments described, said bag comprises a pouch communicating with the exterior by means of projecting tubing. In the unopened condition each tube is arranged inside of a closed compartment and is thus isolated from the external environment. The closure means of the compartment comprise a peelable peripheral weld which is disposed at a distance from the tube. For connecting the tube to a filling or emptying means the two sheets comprising the compartment are separated in order to break the peelable seal. The tube is then completely accessible such that its entire length is exposed to contaminants. In addition, the connection of a tube or tubing to such a tube is rather inconvenient. In fact, it is held in the bag only at one of its ends such that the tubing/bag has no real hold and rigidity, which complicates its connection to a tube or to tubing.

SUMMARY OF THE INVENTION

The object of the present invention is to eliminate these drawbacks.

In other words, it's purpose is to propose a packaging bag that can be attached to an insemination wand without risk of tearing the plastic material of the pouch at the time of performing this operation.

It also proposes enabling performance of this operation under satisfactory conditions; that is, without the risk of disconnection of said wand.

The object of the present invention is also to provide a bag that can be adapted to wand tubes of different diameters under facilitated manipulation conditions and with the likelihood of contamination of the product packaged in the bag being reduced to a minimum.

If the technique utilizing an intermediate coupler is desired, the object of the present invention, while achieving the aforesaid objectives, is to make necessary the one-time use only of said coupler.

Furthermore, the invention proposes achieving all of these objects using simple and inexpensive means.

As stated above, the packaging bag that is the object of this invention is formed of two walls of plastic material joined to each other in such a fashion as to delimit a pouch for receiving substance and, communicating with said pouch, an outlet conduit whose terminal part is, in the absence of a bag opening, closed off by said joined walls.

This bag is essentially remarkable in the fact that it comprises, force fitted in the conduit, a cannula, whose two ends are open and its first end being able to communicate with said pouch, while its second end, disposed in the vicinity of the end part of the conduit, having a conical or more or less conical constriction. It is also notable in that said conduit communicates over a fraction of its length with at least one zone situated not far from the end part, in which the two walls are not joined.

The expression "force-fitted" is defined for the purposes of this description and the claims in that the respective diameters of the conduit and the cannula are such that when said latter is in place, there is perfect tightness between these two elements. In other words, the substance contained in the bag cannot flow out between the conduit and the cannula.

Thus, after having opened the conduit at the level of its end part, access is gained to the second end of the cannula. Being a part that has a rigidity significantly greater than that of the plastic material of the bag, its connection to a wand can be effected under satisfactory conditions without risk of tearing the plastic material of the bag. The cannula being inserted into the conduit, it "captured" so-to-speak such that its connection to the wand is facilitated. Furthermore, having a truncated conical constriction, such a cannula can be adapted to different inside diameters of wand tubes.

In addition, the presence of at least one zone in which the walls of the bag are not joined will facilitate access to the end of the cannula, because the plastic material that initially covers it can be removed.

However, the cannula remains protected and held by the plastic material of the conduit over a considerable part of its length. It is thus protected from contamination from the external environment. Moreover, the cannula is integral with the bag, which confers the assembly with considerable rigidity, further facilitating the connecting of a wand tube.

Finally, due to the fact that the tube of the wand is not introduced directly into the pouch, there is no risk of contamination of the one by the other.

In addition, according to other non-limiting advantageous features of the invention:

- said second end of the cannula abuts or substantially abuts against the end part of the conduit;
- said cannula is made of rigid or semi-rigid material;
- the bag comprises two zones in which the walls are not joined, same being separated from each other by the conduit and opposing each other;
- said cannula has a length greater than that of said conduit such that it extends into or in the direction of said pouch;
- said cannula is capable of sliding into said conduit such that as a consequence of opening of the conduit and a traction operating on the second end of the cannula, it can be extracted by bringing its first end into proximity of the conduit or inside of it;
- the pouch comprises a pair of partitions formed by zones inside of which the two walls are joined, which are interrupted in the vicinity of said conduit and which comprise guiding means of the cannula at the time of its partial extraction;
- said partitions are comprised of aligned sections, separated in pairs;
- said partitions each delimit a compartment in the pouch, said compartments communicate with each other only when the cannula is partially extracted;
- the conduit extends trough a channel, the conduit+channel assembly receiving the cannula and extending alongside the pouch, said pouch communicating with said conduit by way of a conduit and, in the absence of extraction of the cannula, it closes said conduit, so as to prevent the substance from running out of the pouch;
- the assembly formed by said conduit and cannula extending parallel to the major sides of the pouch;
- the bag comprises opening means for the end part of the conduit, said means comprising especially a peelable zone;
- the truncated conical constriction separates two portions of the cannula in which their cross-section is circular and constant, the one closest to the end part having a reduced diameter.

Another aspect of the invention relates to a strip of packaging bags for liquid biological substance, which is comprised of a juxtaposition of bags as described above.

Other features and advantages of the invention will become obvious when reading the following detailed description which will be followed by particular exemplary embodiments.

This description will make reference to the appended drawings, wherein:

Figure 1:
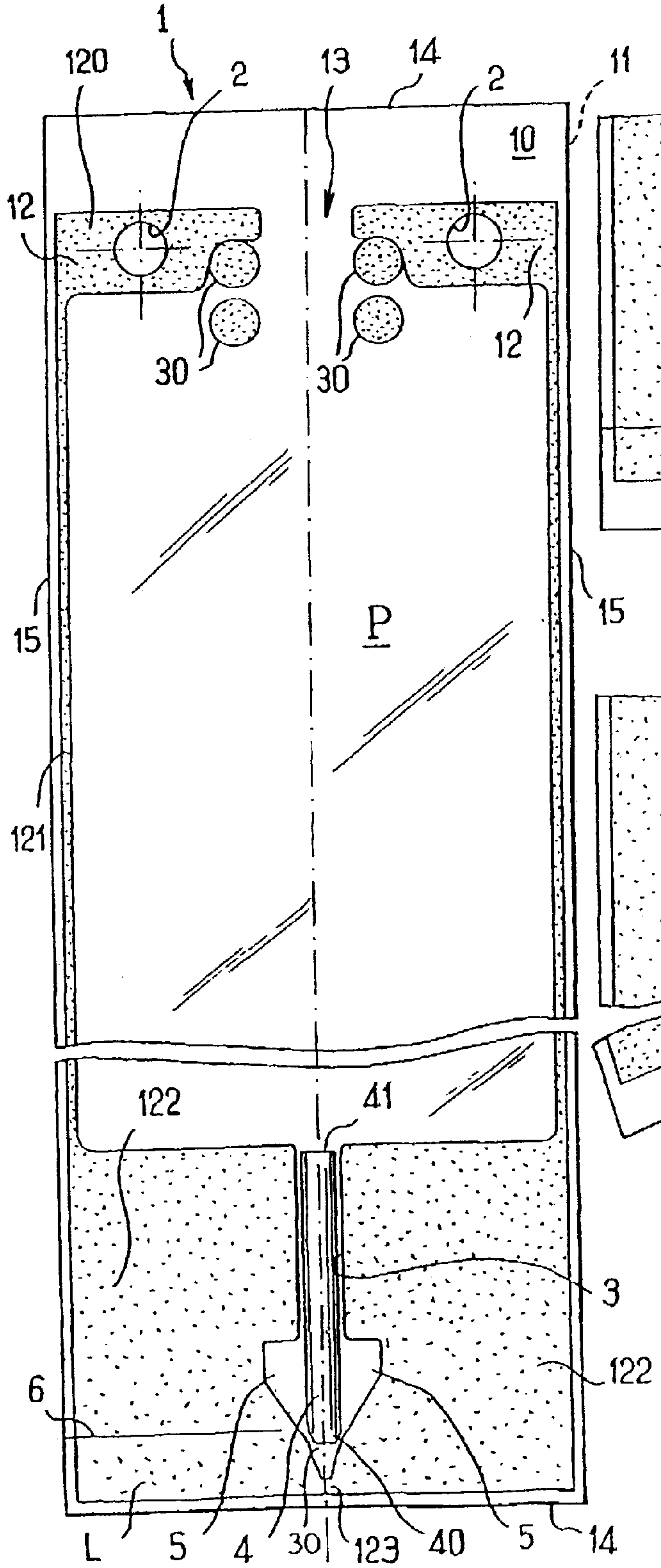
FIG. 1 represents a top view of a packaging bag according to the invention in a first embodiment.

The packaging bag for liquid biological substance represented in FIG. 1 is more particularly for receiving animal semen, especially that of porcine species.

DESCRIPTION OF SOME OF THE EMBODIMENTS

Its overall structure is well known. In this instance, it is comprised of two walls of plastic material 10 and 11 having an elongated rectangular contour. It is a transparent or translucent plastic material such as polyethylene, polyamide or polyethylene terephthalate (PET).

The two walls can be comprised of two distinct sheets or of one single and same sheet folded over itself. Each sheet can be single or multiple layer.

The walls are joined to each other in order to delimit a pouch P for receiving the substance.

In the example represented here, the walls are joined by welding. However, in another embodiment, another method can be used such as adhesives.

The methods are well known by the person skilled in the art and strictly speaking do not constitute part of the invention.

The zones in which the two walls are joined are referenced by 12 and are identified by black dots in the drawings.

In the example represented here, the zones 12 comprise two broad studs 120 that have a generally rectangular shape. They are arranged symmetrically on both ends of the longitudinal median axis of the bag, their major sides extending parallel to the minor sides 14 of the bag. A non-bonded zone extends between them that is indicated by the reference 13 and which comprises an opening for filling the pouch P with the semen. Circular openings 2 capable particularly of enabling the bag to be hung from a stand, for example for filling it, are provided in a central zone of the studs 120.

Underneath the opening 13 and on the inside of the pouch two pair of circular bonded patches 30 extend in the vicinity of the studs 120 and are arranged symmetrically and at either end of the longitudinal median axis of the bag. These patches are for guiding a nozzle (not shown) in the direction of the interior of the pouch, which can be introduced through the opening 13 and used particularly for filling the semen.

The two zones 120 each connect to a thin weld line 121 which extends the vicinity of and parallel to the major sides 15 of the bag. The lines 121 connect in the lower part of the bag with broad studs 122, each inscribing a substantially rectangular shape and communicating with each other in the bottom part by a narrow welded cord 123 in the longitudinal medial axis.

The non-welded surfaces extend between these studs 122. The first connects to the pouch P and is interrupted by the aforesaid zone 123.

It is disposed in the axis of the bag and forms an outlet conduit 3 for the pouch P. This is a perfectly well-known configuration.

In the second instance, two surfaces or zones 5 in which, similarly, the walls are not joined, extend in the bottom part of the conduit 3 at either ends of it and at right angles.

In this case they have a substantially triangular shape.

The respective functions of these zones will be explained in the following.

A cannula 4, preferably made of rigid or semi-rigid plastic, is inserted on the inside of the conduit 3. It is open at its ends, its first end 41 communicating with the pouch P. Its second end 40, disposed in the vicinity of the end part 30 of the conduit 3, has a constriction that confers to it a truncated conical or substantially truncated conical shape. This end part has a tapered shape which forms an extension of the zones 5. Thus, it has a width less than that of the conduit 3.

The diameter of the cannula, apart from the end part, is chosen to be of a dimension such that it can be force-fittingly inserted into the inside of the conduit via the pouch P. Thus, there is no space between the cannula and the conduit such that the semen cannot flow out between them. If required, the cannula can be bonded to the plastic material of the conduit by thermofusion over several millimeters, for example.

The end 40 of the cannula abuts against the converging edges of the end part 30, thus forming a liquid-tight seal.

In the embodiment represented in FIGS. 2 to 8 the zones 5 are rectangular or square.

Figure 10:
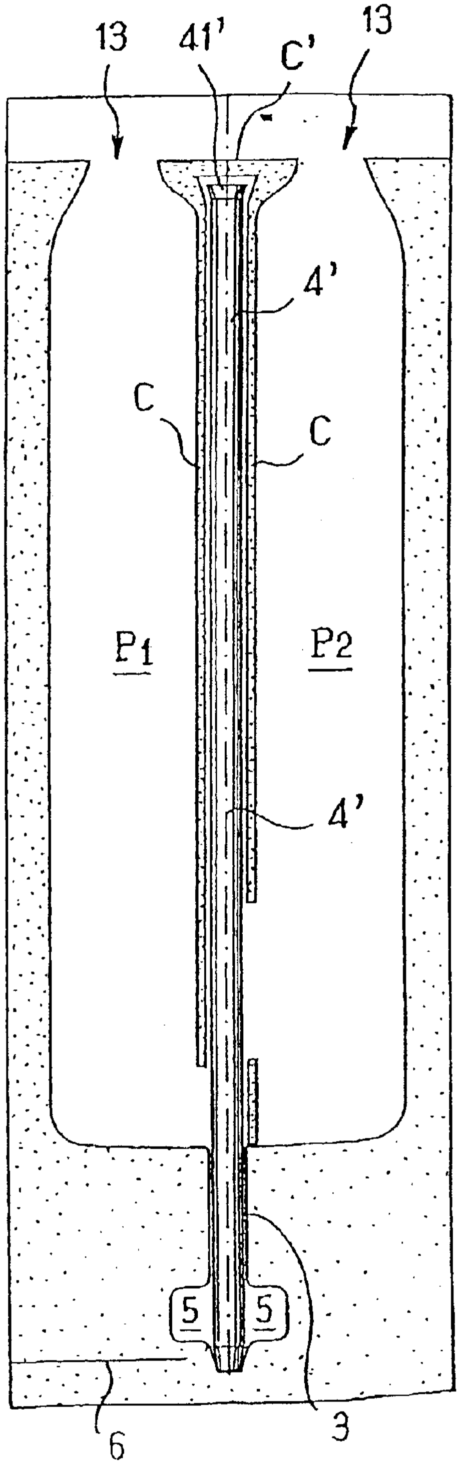
FIG. 10 represents a view from above of another embodiment of the bag.

One further alternative embodiment of the conduit is represented in FIG. 10. In this drawing the two sides of the conduit have been represented in a form that can be disassembled. Of course, they can be identical. Under whatever the circumstances, the wall of the conduit is not contiguous with that of the cannula over its entire length but only in certain zones. These zones are sufficient to assure lateral fitting of the cannula. However, it will be noted that the walls of the conduit 3 are practically sealed with those of the cannula in the end part 41 turned towards the pouch. This is indispensable in preventing the semen from flowing between the conduit and the cannula.

It will be noted that the bag has, at the level of one of the zones 122, and parallel to the minor sides 14, a slit 6. This slit is interrupted in proximity to the end part of the conduit 3, in the immediate proximity to one of the zones 5. It delimits a lower gripping tab L.

The bag represented in FIG. 1 exhibits its condition prior to being filled with semen.

The filling method is of a known type and relatively conventional. It consists essentially of introducing a nozzle into the opening 13 to the inside of the pouch and causing the semen to flow through the nozzle. This operation can be effected manually or it can be mechanized.

When the bag is filled with semen, the opening 13 is then closed, in particular using hot welding. Thus, the pouch is hermetically sealed.

The diameter of the cannula is chosen in such a fashion that the pouch is filled, the semen flows into it. This enables having a better initiation of flow of the semen at the time of the insemination procedure.

The procedure upon opening the bag for the purpose of carrying out an artificial insemination operation will now be explained.

The tab L is gripped, delimited by the slit 6 and a traction effected directed parallel to the minor sides of the bag 14. This results in tearing the plastic material along the line represented in dotted lines in FIG. 2.

Thus, the truncated conical end of the cannula is released by tearing and removing the plastic material covering it.

In an alternative embodiment, it is possible to eliminate the slit 6 and the tab L. This is described more completely with reference to FIG. 12.

Inasmuch as the cannula is flanked by two non-joined zones 5, it is possible to release and lift the plastic tab 100 that initially covers the end of the cannula. The folds formed by the plastic material at the zones 5 and which facilitate release of the tab are indicated by the literal N.

It is thus possible to arrange at the end of the cannula an insemination wand.

The length of the cannula is provided so that the operator can securely hold it in the hand. Thus, for a bag having an overall length of 25 cm, the cannula can measure approximately 3.5 cm or a cannula/bag length ratio of the order of 0.14.

Figure 3:
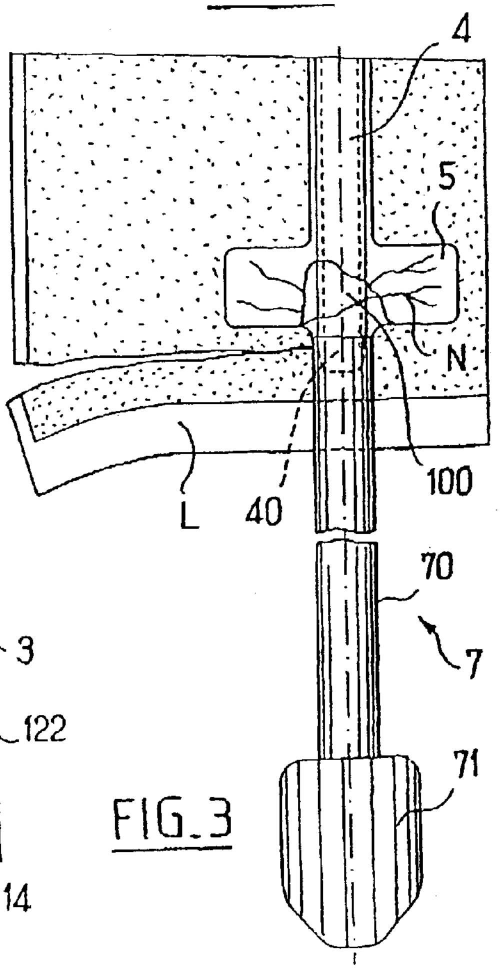
FIG. 3 represents a partial view similar to that of FIG. 2 and intended to show the mode of co-operation of the cannula with an insemination wand after opening of the end part of the conduit.

A simplified exemplary embodiment of such a wand is represented in FIG. 3. It comprises a tube 70 made of semi-rigid plastic material with a plug 71 made of foam material at one of its ends.

The wand is connected to the cannula by its end opposite to the foam plug. This connection is easily done thanks to the particular shape of the end of the cannula, that is, truncated conical.

This shape enables adapting to different wand tube sizes, naturally to the extent where they have an inside tube diameter less than or equal to the exterior diameter of the cannula in it largest part.

This connecting operation is done simply and easily inasmuch as the cannula is considerably more rigid than the plastic material comprising the bag. The connection is made without the risk that the wand disconnects therefrom due to the fact that the plastic material covering the end of the cannula were released by virtue of the zones 5. Finally, because the tube of the wand is not introduced into the inside of the bag, there is no elevated risk of perforation. Consequently, the thickness of the walls 10 and 11 can be reduced. Thus, for example, this thickness can be taken from 90 micrometers to 60 micrometers.

Figures 4, 5:
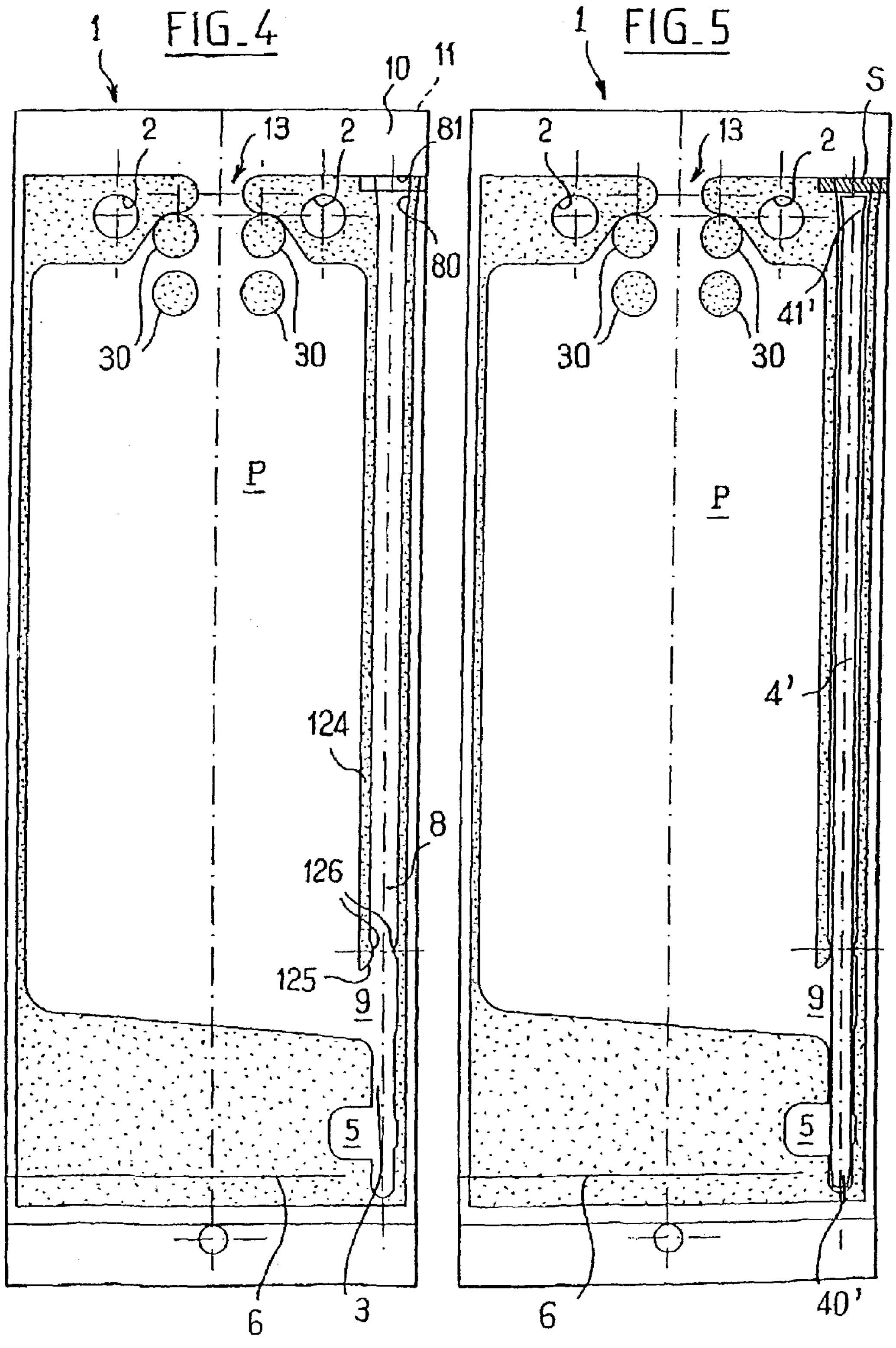
FIGS. 4 and 5 represent top views of a second exemplary embodiment of the bag; however, the cannula, is not shown in FIG. 4.

The bag represented in FIGS. 4 and 5 have the same general appearance as the one represented in FIG. 1. However, in contrast with said latter, its conduit 3 does not extend beyond along the longitudinal medial axis of the bag.

In contrast, it runs along the side of it in the vicinity of and parallel to one of the major sides 15. The pouch P communicates with the conduit by means of an opening 9 disposed in one of its lower corners.

The conduit 3 is extended by a rectilinear channel 9 that extends parallel to the major sides 15. The pouch is separated from the canal by a longitudinal partition 124 where the two walls 10 and 11 are joined. This partition is interrupted to form the communicating opening 9 of the pouch P with the conduit 3.

In this end part, the partition 124 has a greater thickness 126 than the curved profile 125. Its function will be explained below.

Similarly, the weld line turned towards the exterior of the bag also has at this level a overthickness 126.

In the upper part of the bag, the channel 8 has a flared shape with communicates to the outside through a port 81.

Outside of said port 81, the channel has a width greater than that of the conduit 3.

The bag represented in FIG. 5 differs from that of FIG. 4 by the fact that one cannula 4' is represented on the inside of the assembly comprised of the conduit 3 and its extension forming the channel 8.

This cannula 4' has an end 40' with a conical constriction. As in the hereinbefore described example, this end is situated in the vicinity of the lower end part of the conduit 3. At the opposite end 41' the cannula 4' has an expansion.

After introduction of the cannula through the hereinbefore described port 81 it is closed by creating a welded seal (reference S in FIG. 5).

The bag is used as hereinafter described.

Figure 2:
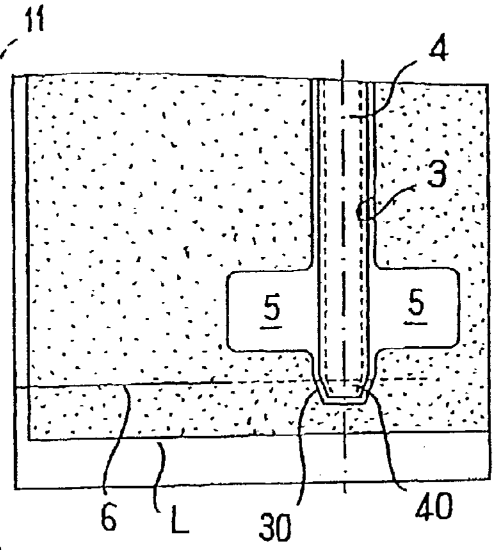
FIG. 2 represents a partial top view of the bottom part of a bag substantially similar to that of FIG. 1 and more specifically the zone where it comprises the outlet conduit.

After opening the bag using the method described with reference to FIGS. 1 to 3, the end of the cannula is gripped in such a fashion as to partially extract it from the bag. The relative dimensions of the cannula and the channel 8 are understood to be chosen so that this connection occurs relatively easily.

Figure 6:
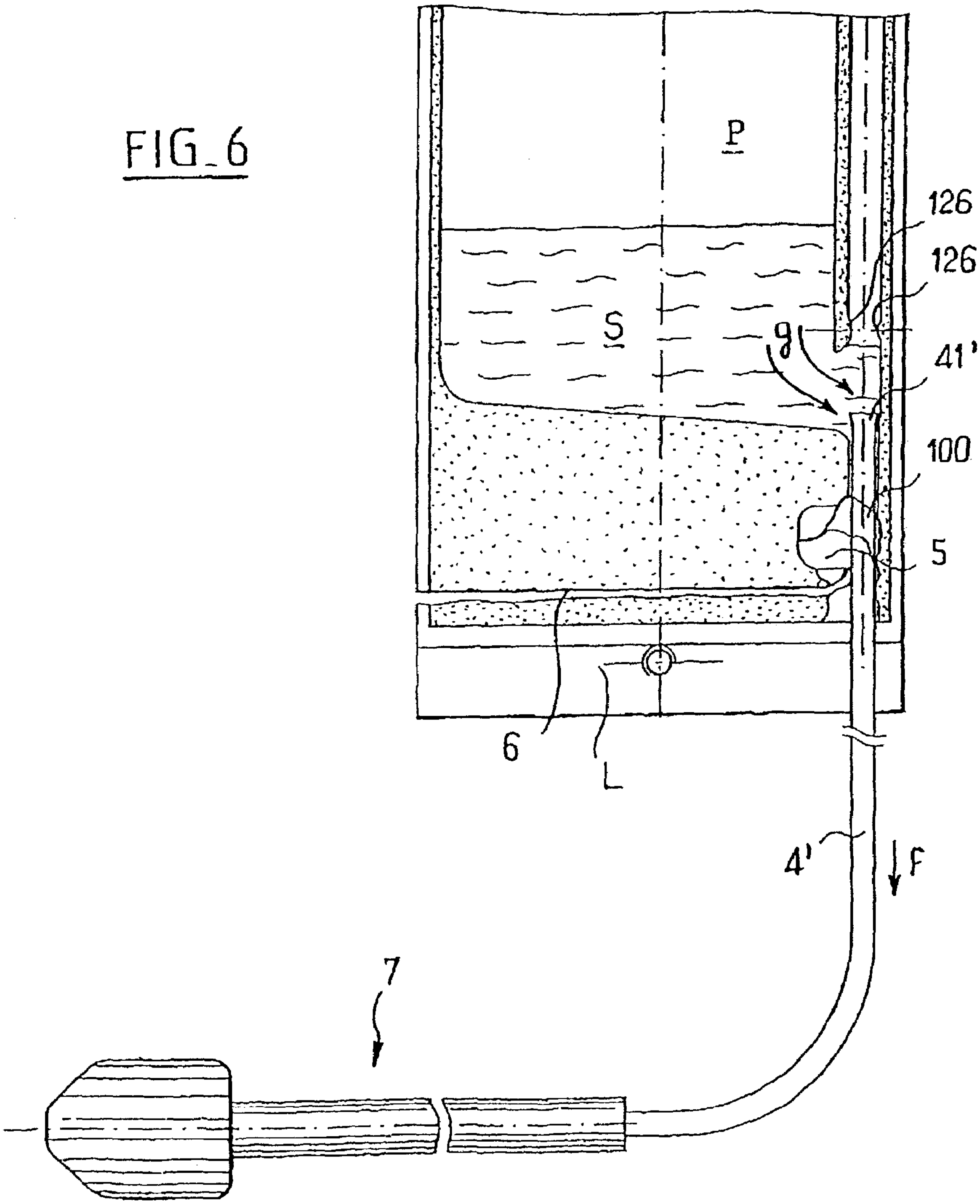
FIG. 6 represents a view intended to show the manner in which the bag of FIGS. 4 and 5 is used.

The direction of extraction of the cannula out of the bag is symbolized by the arrow f in FIG. 6.

Opening of the zone of the overthicknesses is done by the application of a force.

Under whatever circumstances, the flared end of the cannula abuts against the end of the conduit that communicates with the opening 9. Thus, it cannot be extracted entirely from the bag.

The end 40' of the cannula 4' can then be connected to an insemination wand 7. This cannula then acts as a connection similar to those used up to now in the form of independent parts.

However, due to the fact that it is integrated with the inside of the bag, its one-time use is assured. Consequently, the risk of transmitting disease from one animal to another is reduced to zero.

Insemination is achieved by gravitational flow of the semen to the inside of the cannula 4' through the opening 9. The flow of the semen is indicated by the arrows g in FIG. 6.

The fact that the walls of the channel have overthicknesses 126 prevents the semen from migrating to the inside of same by the phenomenon of capillarity.

At the end of insemination and in order to prevent back-flow of the semen to the inside of the pouch P, a slide can be pushed into the cannula 4' in the direction opposite to the arrow f to bring its end 41' up against the overthicknesses 126. The opening is thus closed off.

In this embodiment, the cannula 4' thus has, in addition to its inherent advantages, also those connected with the use of a connector.

Figure 7:
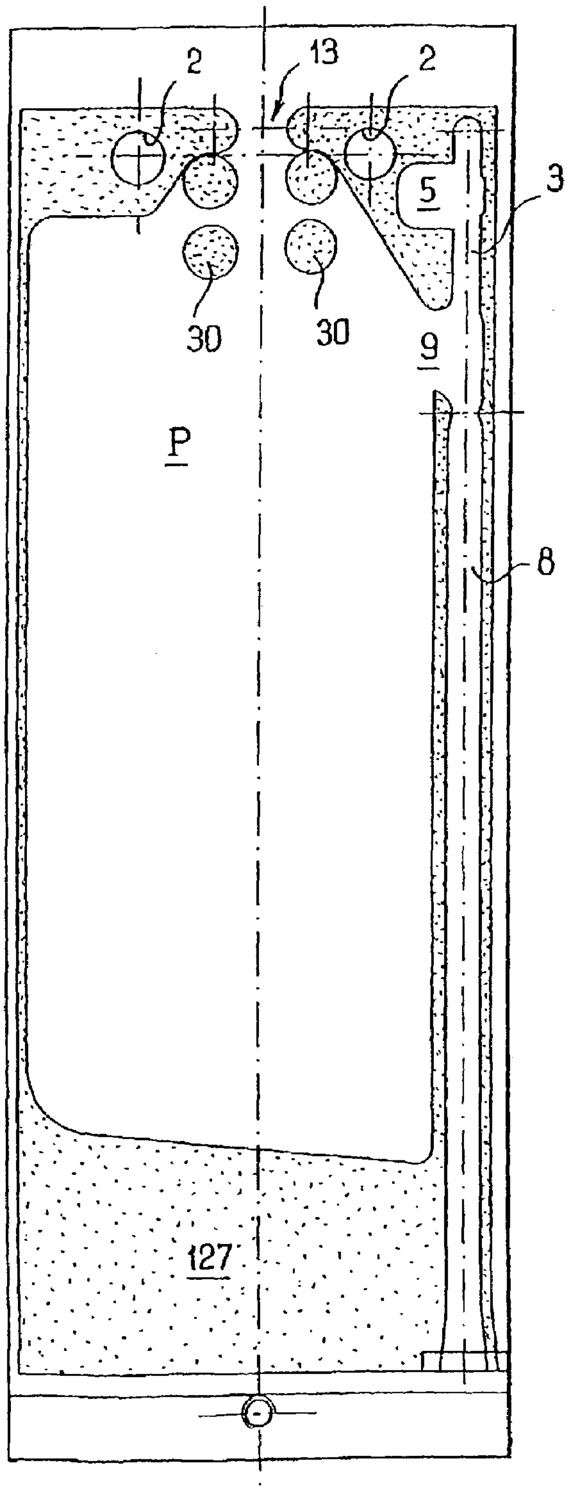
FIGS. 7 and 8 also represent top views of two additional embodiments of the bag according to the invention.

In the embodiment represented in FIG. 7, the conduit 3 and the channel have a reversed position relative to that which they occupy in the aforesaid embodiment. This means that the conduit is open via the minor side 13 of the pouch which also allows its filling.

This enables opening a wide welded zone 127 in the lower part of the bag. According to one embodiment (not shown), the zone can be reduced to a minimum, the space freed up may be occupied by the pouch. This enables especially reducing the width and economizing plastic material.

Figure 8:
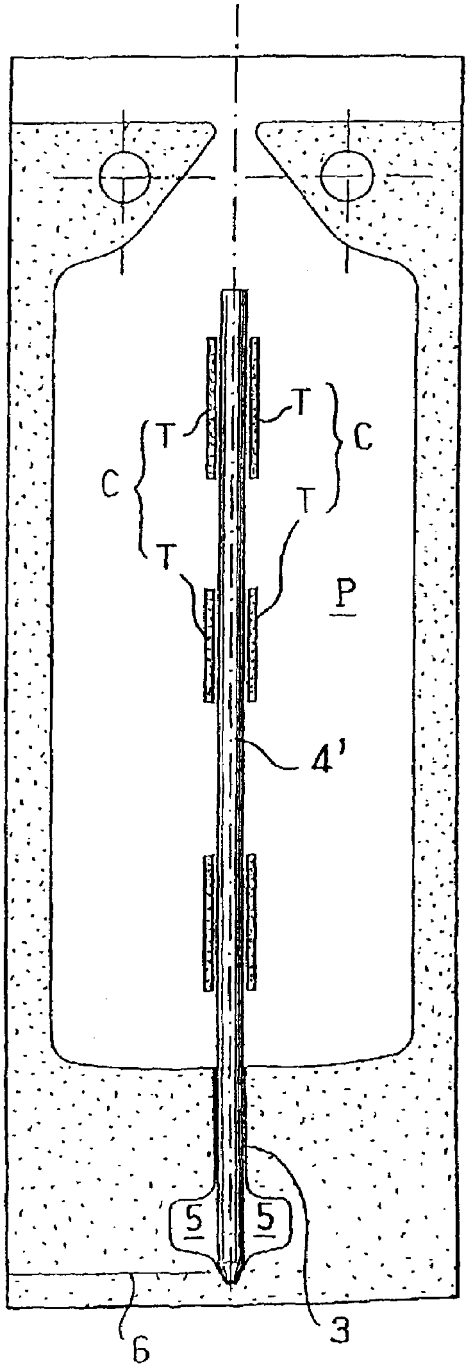
Figure 9:
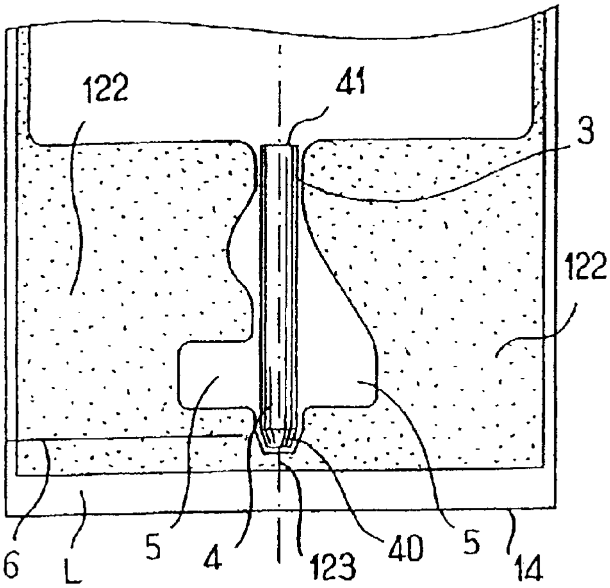
FIG. 9 represents a partial bottom view of the bag of FIG. 1 in a slightly different embodiment.

In the embodiment represented in FIG. 8, the cannula 4' is extending on the inside of the pouch along the longitudinal medial axis of the bag. It is bordered by a series of T sections in which the walls 10 and 11 are joined. Each series forms a fractioned partition C.

The sectors comprise a guiding means when the cannula is partially extracted.

In one embodiment (not shown) the partitions can each be comprised of a single contiguous line in which the walls are joined.

In any case, they have an interruption in the vicinity of the conduit 3 to enable the semen contained in the bag to flow through the cannula.

Finally, the bag represented in FIG. 8 is used in a substantially similar fashion to that of FIGS. 4 to 6.

FIG. 10 represents yet another embodiment of the bag according to the invention. This bag approximates the appearance of the bag described with reference to FIG. 8.

Herein the partitions C that "frame" the cannula are extended in the direction of the top outside of the bag to form a "bridge" C that surrounds its end 41'. On either side of this bridge access ports 13 are arranged to two compartments of the pouch $P_1$ and $P_2$ separated by the cannula 4' and its associated partitions. The partitions each have an interruption for evacuation of the compartments. Said interruptions are offset in height.

These compartments can communicate only when the cannula is partially extracted from the bag; that is, when its end 41' is situated in the vicinity of the conduit 3.

Figure 11:
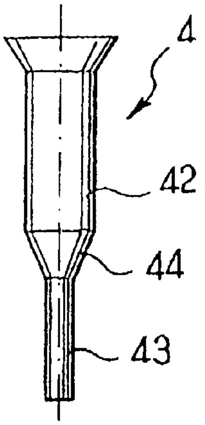
FIG. 11 represents a top view of an alternative embodiment of the cannula.

FIG. 11 represents an additional embodiment of the cannula. The conical constriction 44 framed two parts 42 and 43 in which they have a circular and uniform cross-section. The part 43 has a diameter less than that of the part 42. It is intended to be turned towards the end part of the conduit 3 of the bag. When a wand is connected to the cannula at the level of the zone 44, the part 43 is then engaged in the tube of the wand. The fact that the diameter is reduced enables a slow flow into the wand which provides for a better quality insemination. In the example shown here, the upper portion of the part 42 is flared so as to allow its blockage on translation into the conduit 3.

Figure 12:
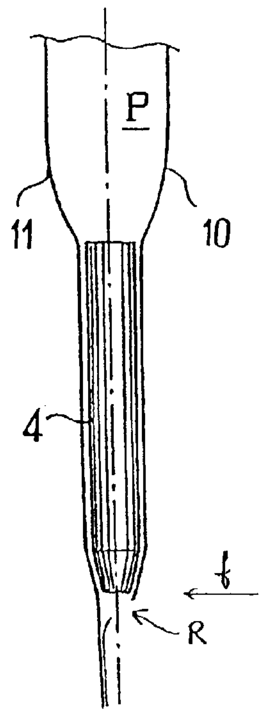
FIG. 12 represents a simplified side view, in partial section, of the bottom part of an alternative of the bag according to the invention, after breaking the plastic material, by the application of a force thereto.

As hereinbefore stated, in the embodiment shown in FIG. 12, the bag does not have a slit 6 or a tab L.

Herein the bag is opened by breaking the plastic material at the level of the lower end of the cannula 4.

More specifically, by a force f applied at the level of the zone 123, in a direction generally perpendicular to the plane of the bag, rupture R of one of the two plastic sheets comprising the bag is caused, especially at the level of the end 40 of the cannula. This phenomenon is explained by the fact that on application of such force, the plastic material of the wall 10 is forced into contact with the peripheral edge of the end 40. The plastic material being retained, because of being welded over the greater part of its surface, it ruptures, and opens the bag at the level of the second end of the cannula.

This opening can be produced when the operator holds the bag in one hand and manipulates the plastic material with the other hand. However, a skilled person can simultaneously hold the bag and open it with one hand.

This cannula thus has a supplementary function: that of providing a tearing tool.

The opening maneuver will be further facilitated if the plastic material used is less rigid but capable of being "broken". A PET/polyethylene complex serves this purpose perfectly; these two materials respectively comprising the outer and inner sides of each wall.

In the examples described herein, the joined zones 5 result from the absence of a weld between the two sheets of plastic that comprise the bag. In one embodiment (not shown) the sheets can be provided with a treatment so that they comprise a "peelable" weld line, which inscribes a right angle on the conduit 3. The term "peelable" as used herein refers to a weld that enables separating the one from the other of the two sheets without affecting integrity. Thus, by installing the cannula 4 in the conduit 3, the sheets are forced to separate locally in the region of the peelable weld in such a fashion that non-joined zones 5 are formed.

The invention claimed is:

1. A packaging bag for a liquid biological substance such as animal semen, comprised of two walls made of plastic material joined in such a manner as to delimit a pouch for receiving said substance and, communicating with said pouch, an evacuation conduit whose end part, in the absence of opening of the bag, is closed by said joined walls, wherein, force-fitted in said conduit, a cannula being able to communicate with said pouch is provided, while a second end of the cannula is situated in the proximity of the end part of the conduit having a conical or substantially conical constriction, and wherein said conduit communicates, over a part of its length, with at least one zone situated not far from the end part, in which the two walls are not joined.

2. The bag according to claim 1, wherein said cannula has a length greater than that of said conduit such that the cannula extends in part at least one of into or in the direction of said pouch.

3. The bag according to claim 2, wherein said cannula is adapted to slide in said conduit in such a fashion so that after opening of the conduit and application of traction operating on the second end of the cannula, the cannula may be partially extracted by bringing its first end into proximity of the conduit or inside the conduit.

4. The bag according to claim 3, wherein the conduit extends into an extension of the pouch, wherein the pouch comprises a pair of partitions formed by zones in which the two walls are joined which are interrupted in the proximity of said conduit and which comprise a guide device for the cannula during partial extraction.

5. The bag according to claim 4, wherein said partitions are comprised of a series of aligned segments.

6. The bag according to claim 4, wherein said partitions each delimit a compartment in the pouch and said compartments communicate with each other solely when the cannula is partially extracted.

7. The bag according to claim 3, wherein the conduit is extended by a channel to form a conduct and channel assembly, the conduit and channel assembly receiving the cannula and extending alongside the pouch, said pouch communicating with said conduit by a port and in the absence of extraction of the cannula, the cannula obstructs said port, thus preventing the substance from flowing out of the pouch.

8. The bag according to claim 7, wherein the pouch has an approximately elongated rectangular shape, wherein the conduct and channel assembly extend parallel to major sides of the pouch.

9. The bag according to claim 1, wherein said second end of the cannula abuts or substantially abuts against the end part of the conduit.

10. The bag according to claim 1, wherein said cannula is formed from a rigid or semi-rigid material.

11. The bag according to claim 1, wherein the bag comprises two zones in which the walls are not joined, the two zones being separated on either side by a conduit and facing each other.

12. The bag according to claim 1, wherein the bag comprises an opening device at the end part of the conduit, said opening device comprising a peelable zone.

13. The bag according to claim 1, wherein the conical constriction separates two portions of the cannula within which their cross-section is circular and substantially constant, the portion closest to the end part of the conduit having a reduced diameter.

* * * * *